United States Patent [19]
Nestler

[11] Patent Number: 5,969,171
[45] Date of Patent: Oct. 19, 1999

[54] METAL COMPLEXES AS BLEACH ACTIVATORS

[75] Inventor: Bernd Nestler, Frankfurt, Germany

[73] Assignee: Clariant GmbH, Frankfurt, Germany

[21] Appl. No.: 09/107,780

[22] Filed: Jun. 30, 1998

[30] Foreign Application Priority Data

Jul. 1, 1997 [DE] Germany ............... 197 28 021

[51] Int. Cl.[6] ............... C07F 13/00; C07F 15/06
[52] U.S. Cl. ............... 556/45; 556/150; 502/155; 510/311; 252/186.33; 252/186.38
[58] Field of Search ............... 556/45, 150; 502/155; 510/311; 252/186.33, 186.38

[56] References Cited

U.S. PATENT DOCUMENTS

| | | | |
|---|---|---|---|
| 2,864,770 | 12/1958 | McCune et al. | 252/138 |
| 2,940,938 | 6/1960 | Blinka | 252/309 |
| 3,368,977 | 2/1968 | Tuvell | 252/137 |
| 3,850,831 | 11/1974 | Hellsten et al. | 252/99 |
| 4,087,369 | 5/1978 | Wevers | 252/102 |
| 4,144,226 | 3/1979 | Crutchfield et al. | 528/231 |
| 4,146,495 | 3/1979 | Crutchfield et al. | 252/89 R |
| 4,399,049 | 8/1983 | Gray et al. | 252/91 |
| 4,583,217 | 4/1986 | Kittel | 370/29 |
| 4,728,455 | 3/1988 | Rerek | 252/99 |
| 4,772,412 | 9/1988 | Green et al. | 252/96 |
| 5,114,606 | 5/1992 | van Vliet et al. | 252/103 |
| 5,114,611 | 5/1992 | Van Kralingen et al. | 252/186.33 |
| 5,244,594 | 9/1993 | Favre et al. | 252/186.33 |
| 5,314,635 | 5/1994 | Hage et al. | 252/102 |

FOREIGN PATENT DOCUMENTS

| | | |
|---|---|---|
| 1102966 | 6/1981 | Canada . |
| 0028849 | 5/1981 | European Pat. Off. . |
| 0240057 | 10/1987 | European Pat. Off. . |
| 0241962 | 10/1987 | European Pat. Off. . |
| 0408131 | 1/1991 | European Pat. Off. . |
| 0458398 | 11/1991 | European Pat. Off. . |
| 0509787 | 10/1992 | European Pat. Off. . |
| 0544440 | 6/1993 | European Pat. Off. . |
| 0544490 | 6/1993 | European Pat. Off. . |
| 0544519 | 6/1993 | European Pat. Off. . |
| 0549272 | 6/1993 | European Pat. Off. . |
| 0630964 | 12/1994 | European Pat. Off. . |
| 0717103 | 6/1996 | European Pat. Off. . |
| 1205711 | 9/1970 | United Kingdom . |
| 1270040 | 4/1972 | United Kingdom . |
| 1292352 | 10/1972 | United Kingdom . |
| 1370377 | 10/1974 | United Kingdom . |
| 1561333 | 2/1980 | United Kingdom . |
| 2194536 | 3/1988 | United Kingdom . |
| WO 95/30681 | 11/1995 | WIPO . |
| WO 96/15136 | 5/1996 | WIPO . |
| WO 97/07191 | 2/1997 | WIPO . |
| WO 97/07192 | 2/1997 | WIPO . |

OTHER PUBLICATIONS

Bertoncello et al., Inorganica Chimica Acta, vol. 174, No. 1, pp. 57–60, 1990.
Derwent Abstracts and Family Patent Reports (1998).
B. Gutkowska, S. Biniecki, Acta Polon. Pharm. 19, 242–249 (1962) [Chem. Abstr. 59, 7425 (1963)].
A. Bittcher et al., Z. Naturforsch.49b, 1089–1100 (1994).
Y.A. Ibrahim, A.H.M. Elwahy, Synthesis 503–508 (1993).

*Primary Examiner*—Porfirio Nazario-Gonzalez
*Attorney, Agent, or Firm*—Miles B. Dearth

[57] ABSTRACT

Metal complexes of the formula 1

$$[L_n M_m X_p]^z Y_q \qquad (1)$$

where
  M is manganese in oxidation state II, III, IV, V and/or VI or cobalt in oxidation state II and/or III or iron in oxidation state II and/or III,
  X is a coordinating or bridging group,
  Y is a counterion in the appropriate stoichiometric amount to compensate an existing charge z, where
  z as the charge of the metal complex can be positive, zero or negative, n and m independently of one another are integers from 1 to 4,
  p is an integer from 0 to 15,
  q is z/charge of Y, and
  L is a ligand of the formula (2), (3) or (4)

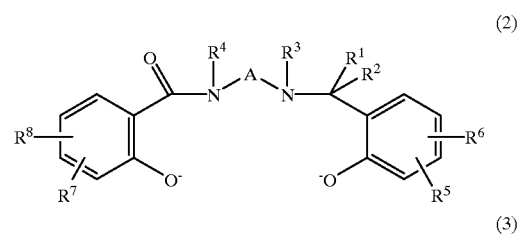

(2)

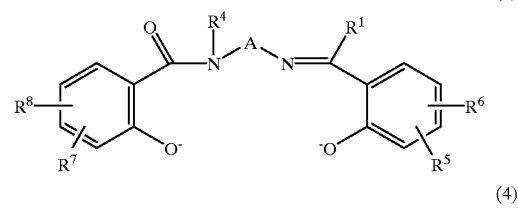

(3)

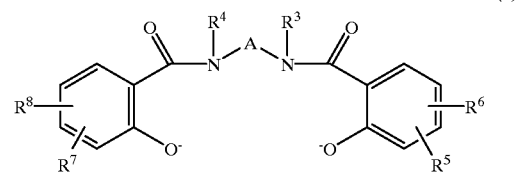

(4)

and A and $R^1$ to $R^8$ are as defined in the description.

11 Claims, No Drawings

METAL COMPLEXES AS BLEACH ACTIVATORS

It is known that the bleaching power of peroxide bleaches in detergents and cleaning products, such as hydrogen peroxide, perborates, percarbonates, persilicates and perphosphates, and hence the efficiency of these bleaches in removing tea, coffee, fruit or red wine stains, only reaches its maximum at relatively high temperatures of distinctly more than 60° C. To improve the bleaching effect, which is greatly reduced at lower temperatures, especially below 60° C., it is possible to employ compounds for activating the peroxide bleaches. A series of transition metal salts or corresponding complexes with mostly chelating compounds has been proposed for this purpose, although the effectiveness of a metal, or of a specific combination of transition metal and complex ligand, cannot be predicted.

Metal complexes of this kind for the activation of peroxy compounds have been described in U.S. Pat. No. 5,314,635, U.S. Pat. No. 5,244,594, U.S. Pat. No 5,114,611, U.S. Pat. No. 5,114,606, U.S. Pat. No. 4,728,455, EP 717 103, EP 6 300 964, EP 549 272, EP 544 519, EP 544 490, EP 544 440, EP 509 787, EP 458 398, EP 408 131, WO 9707191, WO 977192, WO 9615136 and WO 9530681.

The present invention provides new compounds of the formula 1

$$[L_nM_mX_p]Y_q \quad (1)$$

where

M is manganese in oxidation state II, III, IV, V and/or VI or cobalt in oxidation state II and/or III or iron in oxidation state II and/or III, X is a coordinating or bridging group, Y is a counterion in the appropriate stoichiometric amount to compensate an existing charge z, where z as the charge of the metal complex can be positive, zero or negative, n and m independently of one another are integers from 1 to 4, p is an integer from 0 to 15, q is z/charge of Y, and L is a ligand of the formula (2), (3) or (4)

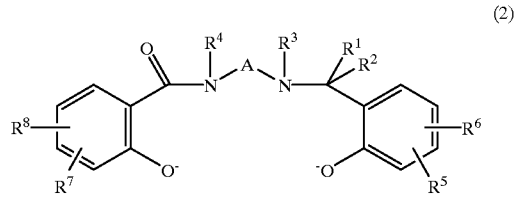

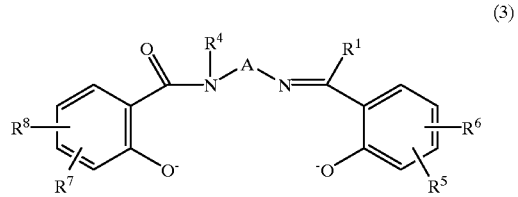

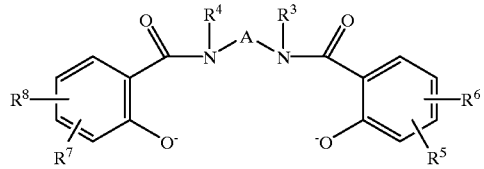

where $R^1$, $R^2$, $R^3$ and $R^4$ independently of one another are hydrogen or a $C_1$- to $C_{10}$-alkyl, cycloalkyl or aryl radical, $R^5$, $R^6$, $R^7$ and $R^8$ independently of one another are hydrogen, $C_1$- to $C_{30}$-alkyl, cycloalkyl or aryl radicals, $C_1$- to $C_4$-alkoxy groups, substituted or unsubstituted amino or ammonium groups, halogen atoms, sulfo groups, carboxyl groups or groups of the formula —$(CH_2)_r$—COOH, —$(CH_2)_r$—$SO_3H$, —$(CH_2)_r$—$PO_3H_2$ or —$(CH_2)_l$—OH where r is an integer from 0 to 4 and I is an integer from 1 to 4 and where said acid groups can also be present in salt form, and A is a $C_2$- to $C_4$-alkylene radical, a $C_5$- to $C_{10}$-cycloalkylene radical or an arylene radical, with the exception of compounds of the formula 1 if L is a ligand of the formula 4, M=Co, Fe, A=ethylene, $R^3$ and $R^4$ are hydrogen and $R^5$ to $R^8$ are chloro.

X is preferably one of the following groups:
$F^-$, $Cl^-$, $Br^-$, $SCN^-$, $OH^-$, $O_2^{2-}$, $O^{2-}$, $O_2^-$, $HOO^-$, $R^9OO^-$, $H_2O$, $SH^-$, $CN^-$, $OCN^-$, $S^{2-}$, $N_3^-$, $NH_3$, $NR^9_3$, $NR^{9-}_2$, $R^9O^-$, $R^9COO^-$, $R^9SO_3^-$ and $R^9SO_4^-$, where $R^9$ is in each case hydrogen, $C_1$- to $C_8$-alkyl, cycloalkyl or $C_6$- to $C_{18}$-aryl. The counterion Y is preferably an ion of the following formulae:

if z is positive: $F^-$, $Cl^-$, $Br^-$, $NO_{3-}$, $ClO_4^-$, $SCN^-$, $PF_6^-$, $R^9SO_4^-$, $R^9COO^-$, $R^9SO_3^-$, $BF_4^-$, $BPh_4^-$, $SO_4^{2-}$ and $SO_4^{2-}$;

if z is negative: $Li^+$, $Na^+$, $K^+$, $Mg^{2+}$, $Ca^{2+}$, $Al^{3+}$, $NH_4^+$, $R^9NH_3^+$, $R^9_2NH_2^+$, $R^9_3NH^+$ and $R^9_4N^+$, where $R^9$ is as defined above.

M is preferably manganese, $R^1$, $R^2$, $R^3$, $R^4$, $R^6$, $R^7$ and $R^8$ are preferably hydrogen, $R^5$ is preferably $C_1$- to $C_4$-alkyl, $C_1$- to $C_4$-alkoxy or a substituted or unsubstituted amino or ammonium group, especially a di-$C_1$- to $C_4$-alkylamino group, and A is preferably ethylene.

The ligands of the formula 4 are obtainable by reacting salicylic acid derivatives, such as the methyl ester, with diaminoalkanes; reactions with N-(2-hydroxybenzyl) diaminoalkanes give ligands of the formula 2; analogous reactions are described in Y. A. Ibrahim, A. H. M. Elwahy, Synthesis 503–508 (1993). An alternative preparation of ligands of the formula 2 is the reduction of ligands of the formula 3, which can be synthesized by reacting N-(2-hydroxybenzoyl)-diaminoalkanes with appropriately substituted salicylaldehydes, in accordance with the details in A. Böttcher et al., Z. Naturforsch. 49b, 1089–1100 (1994). The preparation of the metal complexes of the invention by reaction of Mn, Co or Fe salts with these ligands takes place likewise in accordance with the details in said literature reference.

The monocyclic or polycyclic complexes of the formula 1 of the invention are outstandingly suitable as bleaching and oxidation catalysts, especially in detergents and cleaning products and in the bleaching of textiles and paper.

Particular emphasis here should be placed on textile detergents in the form of powder detergents, or as liquid formulations, and dishwashing compositions. An advantage of the bleaching catalysts of the invention in this context is their stability to hydrolysis and oxidation and also their catalytic effect even at low temperatures. In such formulations they improve the bleaching effect not only of hydrogen peroxide but also of organic and inorganic peroxy compounds.

The present invention accordingly also provides a method of bleaching soiled substrates in which the soiled substrate is brought into contact in an aqueous bleaching liquor with peroxy compounds and an effective amount of one or more of the metal complexes of the invention as bleaching catalysts.

The aqueous bleaching liquor here preferably contains these metal complexes, based on the weight of the bleaching liquor, in an amount of from 0.001 to 100 ppm of metal, in particular from 0.01 to 50 ppm of metal and especially from 0.03 to 20 ppm of metal (ppm being parts per million by weight). Higher contents of metal complexes, for instance up to 500 ppm, may be judicious for industrial bleaching processes, in the textile or paper sector, for example. The low metal contents mentioned to start with relate primarily to household textile detergents.

The invention also provides for the use of these bleaching catalysts in cleaning products and detergents which have a bleaching action. These detergents and cleaning products comprise not only a peroxide compound or a peroxide donor compound and the bleaching catalyst but also, usually, surface-active compounds and further known ingredients.

Suitable peroxides or peroxide donor compounds are alkali metal peroxides, organic peroxides, such as urea-hydrogen peroxide adducts, and inorganic persalts, such as the alkali metal perborates, percarbonates, perphosphates, persilicates and persulfates. Particular preference is given to sodium perborate tetrahydrate and especially to sodium perborate monohydrate. The preference for sodium perborate monohydrate is based on its good stability on storage and on its ready solubility in water. Sodium percarbonate may be preferred on environmental grounds. Alkyl hydroperoxides are a further suitable group of peroxide compounds. Examples of these substances are cumene hydroperoxide and t-butyl hydroperoxide. Aliphatic or aromatic mono- or dipercarboxylic acids and the corresponding salts are other suitable peroxy compounds. Examples of these are peroxy-α-naphthoic acid, peroxylauric acid, peroxystearic acid, N,N-phthaloylaminoperoxycaproic acid, 1,1 2-diperoxydodecanedioic acid, 1,9-diperoxyazelaic acid, diperoxysebacic acid, diperoxyisophthalic acid, 2-decyldiperoxybutane-1,4-dioic acid and 4,4'-sulfonylbisperoxybenzoic acid. Further suitable peroxy compounds are inorganic peroxy acid salts, e.g potassium monopersulfate. Mixtures of two or more of these compounds are likewise suitable.

The detergent and cleaning product formulations of the invention normally comprise from 1 to 30% by weight, in particular from 2 to 25% by weight, of peroxy compounds.

In addition to the peroxy compounds the detergents and cleaning products may additionally include what are known as bleach activators in customary amounts (from about 1 to 10% by weight).

Examples of such bleach activators are compounds having quaternary ammonium structures, such as 2-(N,N,N-triethylammonium)ethyl-4-sulfophenyl carbonate, N-octyl-N,N-dimethyl-N-10-carbophenoxydecylammonium chloride, sodium 3-(N,N,N-trimethylammonium)propyl-4-sulfophenylcarboxylate and N,N,N-trimethylammonium tolyloxybenzenesulfonate.

In addition to the abovementioned quaternary ammonium salts preference is given as bleach activator to esters such as acylphenolsulfonates and acylalkylphenolsulfonates and also acylamides. Of particular interest in this context are the following compounds enthusiastically employed in practice: sodium 4-benzoyloxybenzenesulfonate, N,N,N',N'-tetraacetylethylenediamine (TAED), sodium 1-methyl-2-benzoyloxybenzene-4-sulfonate, sodium 4-methyl-3-benzoyloxybenzoate, sodium nonanoyloxybenzenesulfonate, sodium 3,5,5-trimethylhexanoyloxybenzenesulfonate, benzoylcaprolactam, 2-phenylbenz-(4H)1,3-oxazin-4-one, glucose pentaacetate and tetraacetylxylose, and also ketones and nitrile-type activators.

As an effective amount of the metal complexes of the formula 1 these detergent and cleaning formulations usually include amounts of from 0.0001 to 0.5% by weight of metal, in particular from 0.00025 to 0.25% by weight of metal, especially from 0.0005 to 0.1% by weight of metal, based on the weight of the formulations. These amounts may vary slightly from country to country depending on normal national practice.

The surface-active substance in the detergents and cleaning products may be derived from natural products, such as soap, or is a synthetic compound from the group of anionic, nonionic, amphoteric (zwitterionic) and cationic surface-active substances and mixtures thereof. Many suitable substances are obtainable commercially and are described in the literature; for example, in "Surface active agents and detergents", Vol. 1 and 2 by Schwartz, Perry and Berch. The overall proportion of the surface-active compounds may be up to 50% by weight, preferably from 1 to 40% by weight and, in particular, from 4 to 25% by weight of the overall detergent or cleaning product.

Synthetic anionic surface-active substances are usually water-soluble alkali metal salts of organic sulfates and sulfonates having alkyl radicals of about 8 to 22 carbon atoms, the term "alkyl" including the alkyl substituents of aryl radicals.

Examples of suitable anionic detergents are sodium and ammonium alkylsulfonates, especially the sulfates obtained by sulfating higher ($C_8$ to $C_{18}$) alcohols; sodium and ammonium alkylbenzenesulfonates having an alkyl radical from $C_9$ to $C_{20}$, especially linear secondary sodium alkylbenzenesulfonates having an alkyl radical from $C_{10}$ to $C_{15}$; sodium alkyl glycerol ether sulfates, especially the esters of the higher alcohols derived from tallow oil and coconut oil; the sodium sulfates and sodium sulfonates of coconut fatty acid monoglycerides; sodium and ammonium salts of the sulfuric esters of higher ($C_9$ to $C_{18}$) alkoxylated fatty alcohols, especially of fatty alcohols alkoxylated with ethylene oxide; the products of the esterification reaction of fatty acids with isethionic acid and subsequent neutralization with sodium hydroxide; sodium and ammonium salts of the fatty acid amides of methyl taurine; alkanemonosulfates, such as those from the reaction of α-olefins ($C_8$–$C_{20}$) with sodium bisulfite and those from the reaction of paraffins with $SO_2$ and $Cl_2$ with subsequent basic hydrolysis, which produces a mixture of different sulfonates; sodium and ammonium dialkylsulfosuccinates with alkyl radicals from $C_7$ to $C_{12}$; and olefinsulfonates as formed in the reaction of olefins, especially $C_{10}$ to $C_{20}$ α-olefins, with $SO_3$ and subsequent hydrolysis of the reaction products. The preferred anionic detergents are sodium alkylbenzenesulfonates with alkyl radicals from $C_{15}$ to $C_{18}$, and sodium alkyl ether sulfates with alkyl radicals from $C_8$ to $C_{18}$.

Examples of suitable nonionic surface-active compounds, which are preferably used together with anionic surface-active compounds, are, in particular, the reaction products of alkylene oxides (usually ethylene oxide) with alkylphenols (alkyl radicals from $C_5$ to $C_{22}$), the reaction products generally containing from 5 to 25 ethylene oxide (EO) units in the molecule; the reaction products of aliphatic ($C_8$ to $C_{18}$) primary or secondary, linear or branched alcohols with ethylene oxide, with in general from 6 to 30 EO, and the adducts of ethylene oxide with reaction products of propylene oxide and ethylenediamine. Other nonionic surface-active compounds are alkyl polyglycosides, long-chain tertiary amine oxides, long-chain tertiary phosphine oxides and dialkyl sulfoxides.

Amphoteric or zwitterionic surface-active compounds may likewise be used in the compositions of the invention, although this is usually undesirable owing to their high cost. If amphoteric or zwitterionic compounds are used, they are generally employed in small amounts in compositions predominantly comprising anionic and nonionic surfactants.

Soaps may also be used in the compositions of the invention, preferably with a proportion of less than 25% by weight. They are particularly suitable in small amounts in binary (soap/nonionic surfactant) or in ternary mixtures together with nonionic or mixed synthetic anionic and nonionic surfactants. The soaps used are preferably the sodium salts, and less preferably the potassium salts, of saturated and unsaturated $C_{10}$ to $C_{24}$ fatty acids, or mixtures thereof. The proportions of such soaps may be from 0.5 to 25% by weight, with smaller amounts of from 0.5 to 5% by weight generally being sufficient for foam control. Proportions of soap of between about 2 and about 20%, in particular between about 5 and about 10%, have a positive effect. This is especially the case in hard water, where the soap acts as an additional builder substance.

The detergents and cleaning products generally also include a builder. Suitable builders are calcium-binding substances, precipitants, calcium-specific ion exchangers and mixtures thereof. Examples of calcium-binding substances include alkali metal polyphosphates, such as sodium tripolyphosphate; nitrilotriacetic acid and its water-soluble salts; the alkali metal salts of carboxymethyloxysuccinic, ethylenediaminetetraacetic, oxydisuccinic, mellitic, citric and benzopolycarboxylic acids; and polyacetal carboxylates, as disclosed in U.S. Pat. Nos. 4,144,226 and 4,146,495.

Examples of precipitants are sodium orthophosphate, sodium carbonate and soaps of long-chain fatty acids.

Examples of ion exchangers which are specific for calcium are the various types of water-insoluble, crystalline or amorphous aluminum silicates, of which the zeolites are the best-known representatives.

The builder substances can be present in a proportion of from 5 to 80% by weight, preferably from 10 to 60% by weight.

In addition to the ingredients already mentioned the detergents and cleaning products may include conventional additives in amounts which are commonly encountered in such compositions. Examples of these ingredients are foam formers, such as alkanolamides, especially the monoethanolamides of palm kernel oil fatty acids and coconut fatty acids; foam inhibitors, such as alkyl phosphates and alkylsilicones; antiredeposition agents and similar auxiliaries, such as sodium carboxymethylcellulose and alkyl- or substituted alkylcellulose ethers; stabilizers, such as ethylenediaminetetraacetic acid; softeners for textiles; inorganic salts, such as sodium sulfate; and, usually in small amounts, fluorescent substances, perfumes, enzymes such as proteases, cellulases, lipases and amylases, disinfectants, and colorants. The bleaching catalysts of this invention can be employed in a large number of products. These include textile detergents, textile bleaches, surface cleaners, toilet cleaners, dishwasher cleaning compositions, and also denture cleansers. The detergents may be in solid or liquid form.

It is advantageous for reasons of stability and ease of handling to use the bleach activators in the form of granules which in addition to the bleaching catalyst comprise a binder. Various methods of preparing such granules have been described in the patent literature; for example, in Canadian Pat. No. 1 102 966, GB 1 561 333, U.S. Pat. No. 4,087,369, EP 240 057, EP 241 962, EP 101 634 and EP 62 523.

The granules comprising the bleach catalysts of the invention are generally added to the detergent composition together with the other dry constituents, such as enzymes and inorganic peroxide bleaches. The detergent composition to which the catalyst granules are added can be obtained in various ways, such as by mixing the dry components, extruding or spray-drying.

In another embodiment the bleaching catalysts of the invention are particularly suitable for nonaqueous liquid detergents, together with a bleaching peroxide compound, such as sodium perborate, in order to give the detergent a high cleaning power for fabrics and textiles. Examples of such nonaqueous, liquid detergents, which include pastelike and gelatinous detergent compositions, are described in U.S. Pat. No. 2,864,770, U.S. Pat. No. 2,940,938, U.S. Pat. No. 4,772,412, U.S. Pat. No. 3,368,977, GB 1 205 711, GB 1 370 377, GB 1 270 040, GB 1 292 352, GB 2 194 536, DE 2 233 771 and EP 28 849. They comprise compositions in the form of a nonaqueous liquid medium in which a solid phase may be present in dispersion. The nonaqueous liquid medium can be a liquid surface-active substance, preferably a nonionic surface-active substance, a nonpolar liquid medium such as liquid paraffin, a polar solvent such as a polyol, for example glycerol, sorbitol, ethylene glycol, alone or in conjunction with low molecular mass monohydric alcohols such as ethanol or isopropanol, or mixtures thereof.

The solid phase can consist of builder substances, alkalis, abrasives, polymers and solid ionic surface-active compounds, bleaches, fluorescent substances and other usual solid ingredients.

The examples which follow are intended to give an overview of the embodiments of the invention.

EXAMPLE 1

N-(2-hydroxybenzoyl)-N'-(2-hydroxybenzylidene)-1,2-diaminoethane-manganese complex A solution of 21.6 g of N-(2-hydroxybenzoyl)-1,2-diaminoethane (hydrochloride) (prepared in accordance with: B. Gutkowska, S. Biniecki, Acta Polon. Pharm. 19, 243–249 (1962) [Chem. Abstr. 59, 7425 (1963)]), 12.2 g of salicylaldehyde and 11.0 g of triethylamine in 100 ml of toluene was heated at reflux for three hours. The solvent was removed in vacuo and the residue that remained was washed free from chloride with water and dried in vacuo. Yield: 28.0 g of N-(2-hydroxybenzoyl)-N'-(2-hydroxybenzylidene)-1,2-diaminoethane. 1.14 g of this compound were dissolved in 50 ml of ethanol, and 0.98 g of manganese(II) acetate (tetrahydrate) was added in portions. After heating the mixture under reflux for one hour and then leaving it to stand at room temperature for eight hours, the solvent was removed on a rotary evaporator. The product was extracted from the residue with methylene chloride and was purified by stirring with isopropanol. This gave 1.0 g of N-(2-hydroxybenzoyl)-N'-(2-hydroxybenzylidene)-1,2-diaminoethane-manganese complex in the form of a dark brown amorphous solid.

EXAMPLE 2

N-(2-hydroxybenzoyl)-N'-(2-hydroxybenzylidene)-1,2-diaminoethane-manganese complex The N-(2-hydroxybenzoyl)-N'-(2-hydroxybenzylidene)-1,2-diaminoethane-manganese complex was synthesized as described in Example 1 but using manganese(III) acetate (dihydrate) in the reaction instead of manganese(II) acetate (tetrahydrate).

EXAMPLE 3

N-(2-hydroxybenzoyl)-N'-(2-hydroxybenzyl)-1,2-diaminoethane-manganese complex 11.4 g of methyl salicylate were added dropwise to a solution of 8.31 g of N-(2-hydroxybenzyl)-1,2-diaminoethane [prepared in accordance with: A. Böttcher et al., Z. Naturforsch. 49b, 1089–1100 (1994)] in 50 ml of toluene and the resulting mixture was heated at reflux for 45 minutes. On cooling this mixture a solid was precipitated; this solid was separated off, washed with ethanol/water and dried. This gave 3.59 g of N-(2-hydroxybenzoyl)-N'-(2-hydroxybenzyl)-1,2-diaminoethane. 1.72 g of the resulting compound were dissolved in a mixture of 30 ml of ethanol and 7 ml of dimethylformamide, and 1.49 g of manganese (II) acetate (tetrahydrate) were added in portions. After stirring at boiling heat for three hours the mixture was filtered and the solvent was removed on a rotary evaporator (water pump vacuum). This gave 1.66 g of N-(2-hydroxybenzoyl)-N'-(2-hydroxybenzyl)-1,2-diaminoethane-manganese complex in the form of a dark brown amorphous solid.

EXAMPLE 4

N-(2-hydroxybenzoyl)-N'-(2-hydroxybenzyl)-1,2-diaminoethane-manganese complex

The N-(2-hydroxybenzoyl)-N'-(2-hydroxybenzyl)-1,2-diaminoethane-manganese complex was synthesized as described in Example 3 but using manganese(III) acetate (dihydrate) in the reaction instead of manganese(II) acetate (tetrahydrate).

EXAMPLE 5

N-(2-hydroxybenzoyl)-N'-(3,5-di-tert-butyl-2-hydroxybenzyl)-1,2-diaminoethane-manganese complex Two drops of aqueous sodium hydroxide solution were added to a suspension of 3.96 g of N-(2-hydroxybenzoyl)-N'-(3,5-di-tert-butyl-2-hydroxybenzylidene)-1,2-diaminoethane in 25 ml of ethanol, and 400 mg of sodium borohydride were added in portions at a temperature of 5–10° C. After leaving the mixture to stand at room temperature for 14 h, the solvent was removed in vacuo. The residue obtained was suspended in 50 ml of water, neutralized with dilute hydrochloric acid, filtered off with suction and dried. This gave 3.80 g of N-(2-hydroxybenzoyl)-N'-(3,5-di-tert-butyl-2-hydroxybenzyl)-1,2-diaminoethane.

1.59 g of this compound were dissolved in 40 ml of ethanol, and 980 mg of manganese(II) acetate (tetrahydrate) were added in portions. After the mixture had been refluxed for one hour and left to stand at room temperature for fourteen hours, the solvent was evaporated. The crude product thus obtained was dissolved in 1,2-dichloroethane, the insoluble constituents were separated off, the solvent was removed in vacuo and the residue was washed with petroleum ether. This gave 1.50 g of N-(2-hydroxybenzoyl)-N'-(3,5-di-tert-butyl-2-hydroxybenzyl)-1,2-diaminoethane-manganese complex as a gray-green amorphous solid.

EXAMPLE 6

N,N'-bis-(2-hydroxybenzoyl)-1,2-diaminoethane-manganese complex 1.86 g of manganese(II) acetate (tetrahydrate) were added in portions to a solution of 21.6 g of N,N'-bis-(2-hydroxybenzoyl)-1,2-diaminoethane, [prepared in accordance with: Y. A. Ibrahim, A. H. M. Elwahy, Synthesis 503–508 (1993)] in 30 ml of ethanol and the mixture was heated at reflux for three hours. After the reaction solution had been cooled, the precipitate was separated off, washed with ethanol and dried; this gave 2.88 g of N,N'-bis-(2-hydroxybenzoyl)-1,2-diaminoethane-manganese complex.

EXAMPLE 7

N,N'-bis-(2-hydroxybenzoyl)-1,2-diaminoethane-manganese complex

The N,N'-bis-(2-hydroxybenzoyl)-1,2-diaminoethane-manganese complex was synthesized as described in Example 6 using manganese(III) acetate (dihydrate) in the reaction instead of manganese(II) acetate (tetrahydrate).

The following metal complexes were prepared analogously:

EXAMPLE 8

N-(2-hydroxybenzoyl)-N'-(3,5-di-tert-butyl-2-hydroxybenzylidene)-1,2-diaminoethane-manganese complex

EXAMPLE 9

N-(2-hydroxybenzoyl)-N'-(2-hydroxy-3-methoxybenzylidene)-1,2-diaminoethane-manganese complex

EXAMPLE 10

N-(2-hydroxybenzoyl)-N'-(2-hydroxy-4-methoxybenzylidene)-1,2-diaminoethane-manganese complex

EXAMPLE 11

N-(2-hydroxybenzoyl)-N'-(4-diethylamino-2-hydroxybenzylidene)-1,2-diaminoethane-manganese complex

EXAMPLE 12

N-(2-hydroxybenzoyl)-N'-(2-hydroxy-3-methoxybenzyl)-1,2-diaminoethane-manganese complex

EXAMPLE 13

N-(2-hydroxybenzoyl)-N'-(2-hydroxy-4-methoxybenzyl)-1,2-diaminoethane-manganese complex

EXAMPLE 14

N-(2-hydroxybenzoyl)-N'-(4-diethylamino-2-hydroxybenzyl)-1,2-diaminoethane-cobalt complex Bleaching Experiments A bleach was prepared by combining 200 ml of an aqueous solution of the reference detergent WMP (Krefeld Laundry Research Institute [WFK], 5 g/l in water with 15° dH [German hardness]), 150 mg of sodium perborate monohydrate, 50 mg of tetraacetylethylenediamine (TAED) and 2 mg of the respective catalyst. This composition was used to subject fabric swatches soiled with the standard stain BC-1-tea (WFK) to treatment at a temperature of 40° C. under isothermal washing conditions in a Linitest apparatus (Heraeus). After a washing period of thirty minutes the swatches were rinsed with water, dried and ironed; the bleaching effect was then quantified by determining the difference $\Delta R_{(CAT\text{-}TAED)}$ of the reflectances before and after bleaching, using an ELREPHO 2000 whiteness meter (from Datacolor). These $\Delta R_{(CAT\text{-}TAED)}$ values and the $\Delta R_{(TAED)}$ values obtained in control experiments without a bleaching catalyst were used to calculate the $\Delta\Delta R$ values listed in Table 1, which represent a direct measure of the improvement in bleaching effect induced by the addition of catalyst:

$$\Delta\Delta R = \Delta R_{(Cat\text{-}TAED)} - \Delta R_{(TAED)}$$

TABLE 1

| Catalyst from Example No. | 1 | 3 | 5 | 6 | 8 | 9 | 10 | 11 | 12 | 13 | 14 |
|---|---|---|---|---|---|---|---|---|---|---|---|
| $\Delta\Delta$ R | 2.5 | 4.0 | 3.5 | 3.0 | 2.6 | 2.2 | 2.6 | 4.1 | 4.1 | 4.2 | 3.3 |

Further advantageous properties of the above-described complexes are minimal color deterioration and minimal fiber damage.

I claim:

1. A compound of the formula 1

$$[L_nM_mX_p]Y_q \qquad (1)$$

where

M is manganese in oxidation state II, III, IV, V and/or VI or cobalt in oxidation state II and/or III or iron in oxidation state II and/or III, X is a coordinating or bridging group, Y is a counterion in the appropriate stoichiometric amount to compensate an existing charge z, where z as the charge of the metal complex can be positive, zero or negative, n and m independently of one another are integers from 1 to 4, p is an integer from 0 to 15, q is z/charge of Y, and L is a ligand of the formula (2), (3) or (4)

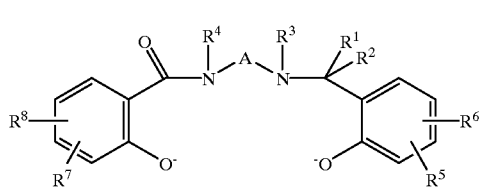

(2)

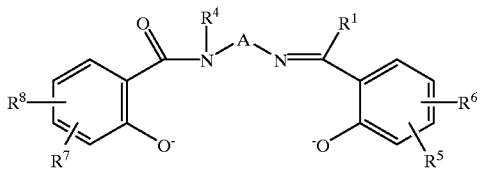

(3)

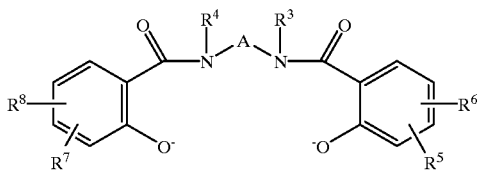

(4)

where $R^1$, $R^2$, $R^3$ and $R^4$ independently of one another are hydrogen or a $C_1$- to $C_{10}$-alkyl, cycloalkyl or aryl radical, $R^5$, $R^6$, $R^7$ and $R^8$ independently of one another are hydrogen, $C_1$- to $C_{30}$-alkyl, cycloalkyl or aryl radicals, $C_1$- to $C_4$-alkoxy groups, substituted or unsubstituted amino or ammonium groups, halogen atoms, sulfo groups, carboxyl groups or groups of the formula $-(CH_2)_I-COOH$, $-(CH_2)_I-SO_3H$, $-(CH_2)_I-PO_3H_2$ or $-(CH_2)_I-OH$ where is an integer from 0 to 4 and I is an integer from 1 to 4 and where said acid groups can also be present in salt form, and A is a $C_2$- to $C_4$-alkylene radical, a $C_5$- to $C_{10}$-cycloalkylene radical or an arylene radical, with the exception of compounds of the formula 1 if L is a ligand of the formula 4, M=Co, Fe, A=ethylene, $R^3$ and $R^4$ are hydrogen and $R^5$ to $R^8$ are chloro and with the exception of compounds of the formula 1 if L is a ligand of the formula 4, M=Mn, A=phenylene, and $R^3$, $R^4$, $R^5$, $R^6$, $R^7$, and $R^8$ are hydrogen.

2. A compound of the formula 1 as claimed in claim 1, where X is $F^-$, $Cl^-$, $Br^-$, $SCN^-$, $OH^-$, $O_2^{2-}$, $O_2^-$, $HOO^-$, $R^9OO^-$, $H_2O$, $SH^-$, $CN^-$, $OCN^-$, $S^{2-}$, $N_3^-$, $NH_3$, $NR^9{}_3$, $NR^9{}_2{}^-$, $R^9O^-$, $R^9COO^-$, $R^9SO_3^-$ or $R^9SO_4^-$, where $R^9$ is in each case hydrogen, $C_1$- to $C_8$-alkyl, cycloalkyl or $C_6$- to $C_{18}$-aryl.

3. A compound of the formula 1 as claimed in claim 1 where the counterion Y is $F^-$, $Cl^-$, $Br^-$, $NO_3^-$, $ClO_4^-$, $SCN^-$, $PF_6^-$, $R^9SO_4^-$, $R^9COO^-$, $R^9SO_3^-$, $BF_4^-$, $BPh_4^-$, $SO_4^{2-}$ and $SO_4^{2-}$; $Li^+$, $Na^+$, $K^+$, $Mg^{2+}$, $Ca^{2+}$, $Al^{3+}$, $NH_4^+$, $R^9NH_3^+$, $R^9{}_2NH_2^+$, $R^9{}_3NH^+$ or $R^9{}_4N^+$ and $R^9$ is as defined in claim 2.

4. A compound of the formula 1 as claimed in claim 1 where M is manganese in oxidation state II, III, IV, V and/or VI, m and n are each 1 or 2 and p is an integer from 0 to 5.

5. A compound of the formula 1 as claimed in claim 1 where M is manganese in oxidation state II and/or III, m and n are each 1 or 2 and p is an integer from 0 to 5.

6. A compound of the formula 1 as claimed in claim 1 where M is manganese in oxidation state II, III, IV, V and/or VI, m and n are each 1 and p is an integer from 0 to 3.

7. A compound of the formula 1 as claimed in claim 1 where M is manganese in oxidation state II and/or III, m and n are each 1 and p is an integer from 0 to 3.

8. A compound of the formula 1 as claimed in claim 1 where M is manganese in oxidation state II, III, IV, V and/or VI, m and n are each 1 and p is zero.

9. A process for bleaching comprising the use of a bleach in combination with the compound of the formula 1 as a bleaching catalyst, said compound having the following structure:

$[L_nM_mX_p]^zY_q$ (1)

where
M is manganese in oxidation state II, III, IV, V and/or VI or cobalt in oxidation state II and/or III or iron in oxidation state II and/or III,
X is a coordinating or bridging group,
Y is a counterion in the appropriate stoichiometric amount to compensate an existing charge z, where
z as the charge of the metal complex can be positive, zero or negative,
n and m independently of one another are integers from 1 to 4,
p is an integer from 0 to 15,
q is z/charge of Y, and
L is a ligand of the formula (2), (3) or (4)

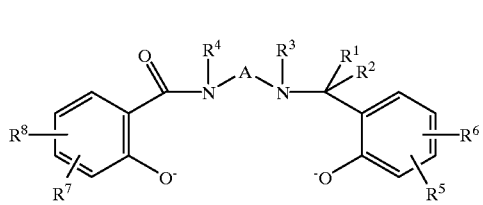

(2)

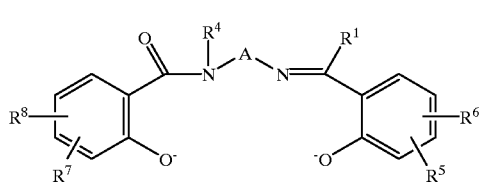

(3)

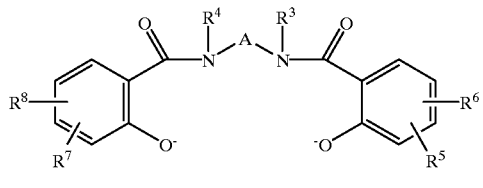

(4)

where
$R^1$, $R^2$, $R^3$ and $R^4$ independently of one another are hydrogen or a $C_1$- to $CO_{10}$-alkyl, cycloalkyl or aryl radical,
$R^5$, $R^6$, $R^7$ and $R^8$ independently of one another are hydrogen, $C_1$- to $C_{30}$-alkyl, cycloalkyl or aryl radicals, $C_1$- to $C_4$-alkoxy groups, substituted or unsubstituted amino or ammonium groups, halogen atoms, sulfo groups, carboxyl groups or groups of the formula —$(CH_2)_r$—COOH, —$(CH_2)_r$—$SO_3H$, —$(CH_2)_r$—$PO_3H_2$ or —$(CH_2)_I$—OH where r is an integer from 0 to 4 and I is an integer from 1 to 4 and where said acid groups can also be present in salt form, and
A is a $C_2$- to $C_4$-alkylene radical, a $C_5$- to $CO_{10}$-cycloalkylone radical or an arylene radical,
with the exception of compounds of the formula 1 if L is a ligand of the formula 4, M=Co, Fe, A=ethylene, $R^3$ and $R^4$ are hydrogen and $R^5$ to $R^8$ are chloro.

10. A process for imparting a bleaching catalyst or oxidation catalyst function into detergents or cleaning products comprising employing in said detergents or cleaning products the compound of the formula 1:

$[L_nM_mX_p]^zY_q$ (1)

where
M is manganese in oxidation state II, III, IV, V and/or VI or cobalt in oxidation state II and/or III or iron in oxidation state II and/or III,
X is a coordinating or bridging group,
Y is a counterion in the appropriate stoichiometric amount to compensate an existing charge z, where
z as the charge of the metal complex can be positive, zero or negative,
n and m independently of one another are integers from 1 to 4,
p is an integer from 0 to 15,
q is z/charge of Y, and
L is a ligand of the formula (2), (3) or (4)

(2)

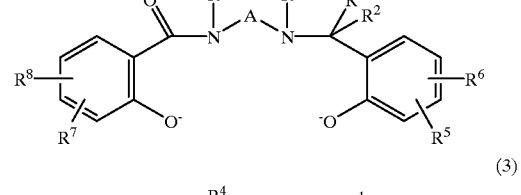

(3)

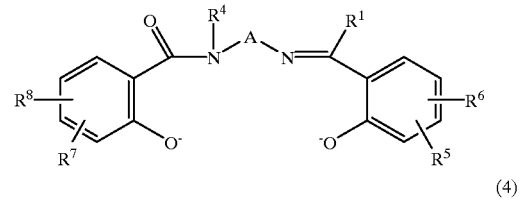

(4)

where
$R^1$, $R^2$, $R^3$ and $R^4$ independently of one another are hydrogen or a $C_1$- to $C_{10}$-alkyl, cycloalkyl or aryl radical,
$R^5$, $R^6$, $R^7$ and $R^8$ independently of one another are hydrogen, $C_1$- to $C_{30}$-alkyl, cycloalkyl or aryl radicals, $C_1$- to $C_4$-alkoxy groups, substituted or unsubstituted amino or ammonium groups, halogen atoms, sulfo groups, carboxyl groups or groups of the formula —$(CH_2)_r$—COOH, —$(CH_2)_r$—$SO_3H$, —$(CH_2)_r$—$PO_3H_2$ or —$(CH_2)_I$—OH where r is an integer from 0 to 4 and I is an integer from 1 to 4 and where said acid groups can also be present in salt form, and
A is a $C_2$- to $C_4$-alkylene radical, a $C_5$- to $C_{10}$-cycloalkylone radical or an arylene radical,
with the exception of compounds of the formula 1 if L is a ligand of the formula 4, M=Co, Fe, A=ethylene, $R^3$ and $R^4$ are hydrogen and $R^5$ to $R^8$ are chloro.

11. The process for bleaching textiles or paper comprising treating said textiles or paper with a bleach containing the compound having the formula 1:

$[L_nM_mX_p]^zY_q$ (1)

where
M is manganese in oxidation state II, III, IV, V and/or VI or cobalt in oxidation state II and/or III or iron in oxidation state II and/or III, X is a coordinating or bridging group, Y is a counterion in the appropriate stoichiometric amount to compensate an existing charge z, where z as the charge of the metal complex can be positive, zero or negative, n and m independently of one another are integers from 1 to 4, p is an integer from 0 to 15, q is z/charge of Y, and L is a ligand of the formula (2), (3) or (4)

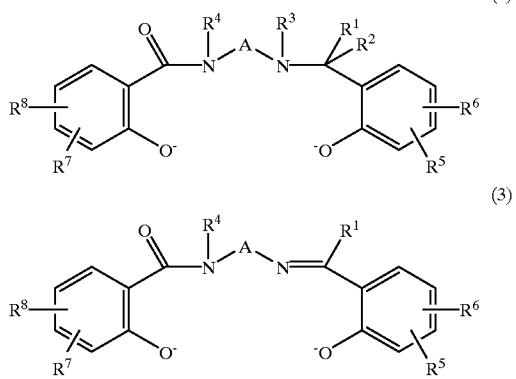

(2)

(3)

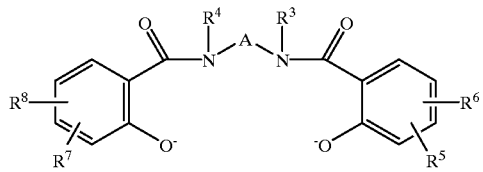

(4)

where $R^1$, $R^2$, $R^3$ and $R^4$ independently of one another are hydrogen or a $C_1$- to $C_{10}$-alkyl, cycloalkyl or aryl radical, $R^5$, $R^6$, $R^7$ and $R^8$ independently of one another are hydrogen, $C_1$- to $C_{30}$-alkyl, cycloalkyl or aryl radicals, $C_1$- to $C_4$-alkoxy groups, substituted or unsubstituted amino or ammonium groups, halogen atoms, sulfo groups, carboxyl groups or groups of the formula —$(CH_2)_r$—COOH, —$(CH_2)_r$—$SO_3H$, —$(CH_2)_r$—$PO_3H_2$ or —$(CH_2)_l$—OH where r is an integer from 0 to 4 and I is an integer from 1 to 4 and where said acid groups can also be present in salt form, and A is a $C_2$- to $C_4$-alkylene radical, a $C_5$- to $C_{10}$-cycloalkylene radical or an arylene radical, with the exception of compounds of the formula 1 if L is a ligand of the formula 4, M=Co, Fe, A=ethylene, $R^3$ and $R^4$ are hydrogen and $R^5$ to $R^8$ are chloro.

\* \* \* \* \*